United States Patent

Holm et al.

[19]

[11] Patent Number: 5,824,230
[45] Date of Patent: Oct. 20, 1998

[54] METHOD AND DEVICE FOR SEPARATING A COMPONENT SUCH AS FIBRIN I FROM BLOOD PLASMA

[75] Inventors: Niels Erik Holm, Birkerød, Denmark; Peter A. D. Edwardson, Chester, United Kingdom

[73] Assignee: E.R. Squibb & Sons, Inc., Princeton, N.J.

[21] Appl. No.: 745,119

[22] Filed: Nov. 7, 1996

Related U.S. Application Data

[60] Division of Ser. No. 566,348, Dec. 1, 1995, Pat. No. 5,738,784, which is a continuation-in-part of Ser. No. 348,668, Dec. 2, 1994, abandoned.

[51] Int. Cl.[6] .................................................. B01D 21/26
[52] U.S. Cl. .......................... 210/749; 210/782; 210/787; 422/72; 422/101; 435/13; 436/177; 494/36; 530/381; 530/382
[58] Field of Search ................................ 210/198.1, 199, 210/206, 210, 360.1, 380.1, 645, 749, 782, 787; 422/72, 101; 435/13; 436/177; 494/36; 530/381, 382

[56] References Cited

U.S. PATENT DOCUMENTS

| | | |
|---|---|---|
| 3,064,647 | 11/1962 | Earl . |
| 3,078,847 | 2/1963 | Wandell et al. . |
| 3,799,342 | 3/1974 | Greenspan . |
| 3,908,893 | 9/1975 | Williams . |
| 3,911,918 | 10/1975 | Turner . |
| 3,932,277 | 1/1976 | McDermott et al. . |
| 4,086,924 | 5/1978 | Latham, Jr. . |
| 4,141,887 | 2/1979 | Seufert . |
| 4,300,717 | 11/1981 | Latham, Jr. . |
| 4,359,049 | 11/1982 | Redl et al. . |
| 4,471,888 | 9/1984 | Herb et al. . |
| 4,530,691 | 7/1985 | Brown . |
| 4,566,610 | 1/1986 | Herb . |

(List continued on next page.)

FOREIGN PATENT DOCUMENTS

| | | |
|---|---|---|
| 0446713 | 2/1991 | European Pat. Off. . |
| 0505962 | 3/1992 | European Pat. Off. . |
| 0 592 242 A1 | 4/1994 | European Pat. Off. . |
| 0 654 669 A2 | 5/1995 | European Pat. Off. . |
| 3920694 | of 0000 | Germany . |

*Primary Examiner*—David A. Reifsnyder
*Attorney, Agent, or Firm*—Theodore R. Furman, Jr.; John M. Kilcoyne; Stuart E. Krieger

[57] ABSTRACT

A method and a device for separating a component, such as fibrin monomer from blood, by centrifugation, involve feeding of blood admixed an anticoagulant to a first annular chamber in a device, where the annular chamber is defined by a cylindrical outer wall and a cylindrical inner wall, both walls extending coaxially about a common axis, as well as by a top wall and a bottom wall. The top wall or the bottom wall is formed by a piston body displaceable within the first chamber. This method involves furthermore a centrifugation of the device about the said common axis to substantially separate blood into a cell fraction and a plasma fraction followed by the resulting plasma fraction being transferred while influenced by the piston body to a second chamber defined by an outer cylindrical wall. The outer cylindrical wall extends coaxially with the said common axis, whereby a fraction with fibrin I is caused to be separated in the second chamber while a suitable enzyme is being added. The separation of fibrin monomer from the plasma fraction in the second chamber is carried out during continued centrifugation whereby a fibrin polymer is deposited on the cylindrical outer wall of said second chamber, whereafter the fluid fraction collected at the bottom of the second chamber is transferred while influenced by the piston body to the first chamber. The fraction with fibrin polymer remaining in the second chamber is substantially deposited on the cylindrical wall and is caused to be dissolved by addition of a solvent and by centrifugation, whereafter it is transferred to a receiving container by passing after addition of a binder to the enzyme through a filter removing said enzyme, whereby a fibrin monomer containing solution is provided.

29 Claims, 3 Drawing Sheets

U.S. PATENT DOCUMENTS

| | | |
|---|---|---|
| 4,596,657 | 6/1986 | Wisdom . |
| 4,666,429 | 5/1987 | Stone . |
| 4,668,399 | 5/1987 | Duggins . |
| 4,729,829 | 3/1988 | Duggins . |
| 4,735,726 | 4/1988 | Duggins . |
| 4,767,396 | 8/1988 | Powers . |
| 4,784,157 | 11/1988 | Halls et al. . |
| 4,795,441 | 1/1989 | Bhatt . |
| 4,810,378 | 3/1989 | Carmen et al. . |
| 4,818,386 | 4/1989 | Burns . |
| 4,828,716 | 5/1989 | McEwen et al. . |
| 4,902,281 | 2/1990 | Avoy . |
| 4,934,827 | 6/1990 | Taschke . |
| 5,030,215 | 7/1991 | Morse et al. . |
| 5,061,381 | 10/1991 | Burd . |
| 5,100,372 | 3/1992 | Headley . |
| 5,137,181 | 8/1992 | Keller . |

METHOD AND DEVICE FOR SEPARATING A COMPONENT SUCH AS FIBRIN I FROM BLOOD PLASMA

This is a divisional of Application Ser. No. 08/566,348 filed Dec. 1, 1995 now U.S. Pat. No. 5,738,784 which is a continuation-in-part of U.S. Ser. No. 08/348,668 filed Dec. 2, 1994 now abandoned.

TECHNICAL FIELD

The invention relates to a method for separating a component, such as fibrin monomer from plasma, said method involving feeding of plasma to a second chamber defined by a wall, whereafter a fraction with non-crosslinked fibrin polymer is caused to be separated while a suitable enzyme is being added.

BACKGROUND ART

EP-PS No. 592,242 describes methods and compositions for a completely novel fibrin sealant involving contacting a desired site with a composition comprising fibrin monomer and converting this monomer to a fibrin polymer concurrently with the contacting step. The term "fibrin" is defined as fibrin I, fibrin II, and/or des ββ fibrin.

Further methods and devices are known from EP 0 654 669 for separating a component, such as fibrin monomer from blood. Such methods for separating the components of a liquid containing several components of a varying specific gravities involves the steps of the blood being collected in a first chamber of a device, said chamber being defined by a substantially axially symmetrical outer and inner wall. The blood is subjected to a centrifugation by way of rotation of the device about the axis of symmetry of the chamber so as to establish a concentric interface between the components of the blood. At least one of the components of the blood, such as plasma is subsequently transferred to a second chamber in the device preferably by way of reduction of the volume of the first chamber during a continued centrifugation of the device. The substantially axially symmetrical inner wall is provided in the first chamber so as to ensure that all the blood is subjected to a centrifugal rotation necessary for the separation. This inner wall is of a radius adapted to the desired speed of rotation such that a sufficient centrifugal force is provided at all locations of the chamber to maintain this concentric separation.

In the second chamber a fraction with non-crosslinked fibrin polymer is separated from the plasma by means of a suitable enzyme and subsequently redissolved into fibrin monomer and transferred to a syringe through a filter by reducing the volume of the second chamber.

It turned out, however, that the separation of a component, such as fibrin monomer from blood, only by way of filtration in a device of the above type does not provide a satisfying result. This is mainly due to the fact that it is difficult to ensure a satisfying separation of the fraction containing fibrin monomer in the second chamber, and accordingly a relatively high amount of the content in the blood of fibrin is lost during the following transfer of a fluid fraction from the second chamber to the first chamber during the succeeding step of the method.

Also, in the earlier fibrin monomer method, the above-described treatment of fibrinogen within the plasma with a suitable enzyme produced the non-crosslinked fibrin polymer in the form of a thick gel mass at the bottom of the second chamber. To provide the desired fibrin monomer solution, a significant amount of redissolving buffer combined with substantial agitation was required. This resulted in several drawbacks. First, preferred fibrin monomer methods, e.g., for use as a fibrin sealant as in EP 592,242, require concentrated fibrin monomer solutions, and the large amount of redissolving buffer or solvent required to dissolve the gel mass provided dilute solutions which do not work as well. Further, the substantial agitation required to dissolve the gel mass into a fibrin monomer solution can cause damage to the device and to the fibrin itself.

SUMMARY OF THE INVENTION

An object of the invention is therefore to provide a method allowing an improved separation of a component such as fibrin monomer from blood.

This invention includes a method which provides for the separation of non-crosslinked fibrin polymer from a plasma fraction in a cylindrical chamber, such separation being carried out during centrifugation whereby the non-crosslinked fibrin polymer is deposited on the outer wall of the chamber, whereafter the remaining fluid fraction collected in the chamber is removed from the chamber, and that the fraction with non-crosslinked fibrin polymer remaining in the chamber substantially deposited on the wall is caused to be dissolved by addition of a solvent and by centrifugal agitation.

Since the treatment of the plasma with the enzyme is carried out during continued centrifugation, the centrifugal force upon the resulting non-crosslinked fibrin polymer provides that it is precipitated as a thin gel film which substantially sticks to the circumferential walls of the chamber. The remaining plasma liquid deposits at the bottom of the chamber when the centrifugation is stopped and can be removed by any convenient means. The desired fibrin monomer solution is thereafter provided by introducing a suitable redissolving buffer solution into the chamber and subjecting the buffer in the gel-coated chamber to centrifugal agitation. This method provides advantages over prior methods. First, the redissolving of the non-crosslinked gel by the buffer solution is extremely efficient due in part to the large surface area of the same volume of fibrin gel compared to the fibrin gel mass provided in prior methods. Accordingly, the gel can be dissolved with small amounts of redissolving buffer resulting in a desirably concentrated fibrin monomer solution. Further, the action of the centrifugal agitation on the buffer solution within the gel-coated chamber is a comparatively gentle method causing no damage to the equipment or to the fibrin monomer product. The resulting high concentration fibrin monomer solution is in the range of 10–30 mg of fibrin monomer per ml of solution and preferably about 25 mg/ml.

This invention also includes a method involving feeding of blood preferably in the presence of an anticoagulant to a first annular chamber in a device, where the annular chamber is defined by a cylindrical outer wall and a cylindrical inner wall, both walls extending coaxially about a common axis, as well as by a top wall and a bottom wall, where the top wall or the bottom wall is formed by a piston body displaceable within the first chamber, which method further involving a centrifugation of the device about the said common axis to substantially separate blood into a cell fraction and a plasma fraction followed by the resulting plasma fraction being transferred while influenced by the piston body to a second chamber defined by an outer cylindrical wall, which extends coaxially with the common axis, whereby a fraction with non-crosslinked fibrin polymer is caused to be separated in the second chamber while a suitable enzyme is being added.

According to the invention this method is characterized in that the fibrinogen-containing plasma fraction is subjected to the enzyme during centrifugation so that the resulting non-crosslinked fibrin polymer is deposited on the cylindrical outer wall of the second chamber, whereafter the fluid fraction collected at the bottom of the second chamber is transferred while influenced by the piston body to the first chamber, and that the fraction with non-crosslinked fibrin polymer remaining in the second chamber substantially deposited on the cylindrical wall is caused to be dissolved by addition of a solvent and by centrifugal agitation. Thereafter the enzyme can be removed, if desired, and the so-produced fibrin monomer solution is transferred to any desired receiving container.

Accordingly, an aseptic condition for collecting the solution is easily maintained. After the fibrin monomer has been redissolved, it can be transferred to a receiving container, such as a syringe for further use as described in the prior art. Before the transfer, the enzyme can be removed by any convenient means.

A device for separating components from a liquid by way of centrifugation about a central axis of rotation comprises a first annular chamber defined by an outer cylindrical wall and an inner cylindrical wall, both walls being concentrically accommodated about the axis of rotation, as well as by a top wall and a bottom wall, where the bottom wall is formed by a piston body displaceable within the first chamber. The device further comprises a second chamber communicating with the first chamber through a first conduit where the second chamber is defined by an outer cylindrical wall concentrically accommodated about the axis of rotation and by the piston body and a bottom wall, where the second chamber is adapted to be portioned below the first chamber during the centrifugation, and where the device also comprises blood feeding means for feeding blood to the first chamber and composition feeding means for feeding composition promoting the separation as well as receiving means for the connection of at least one liquid-receiving container, where the receiving means communicate with the second chamber through a second conduit. In a preferred embodiment, the piston rod comprises the inner wall of the first chamber.

This inventive device for carrying out the method according to the invention is characterized in that the first conduit comprises at least one channel extending between an opening at the top wall of the first chamber and an opening at the bottom wall of the second chamber.

As a result a device is provided which is relatively simple and which independent of the position of the piston ensures an easy and fast transfer of the fractions in question from one chamber to the other chamber, and especially of the fluid fraction from the second chamber to the first chamber after the separation of the fibrin-I-containing fraction. The latter is especially due to the fact that the fluid is automatically concentrated at the bottom of the second chamber when the centrifugation is stopped, whereby it can be easily transferred to the first chamber by the piston being moved, e.g., by compressing air within the second chamber so as to force the fluid up the transfer channel.

According to the invention it is particularly preferred that the channel extends through the interior of the outer cylindrical wall in both the first and the second chamber with the result that the device is particularly simple and easy to manufacture.

According to the invention the opening of the one or more channels at the bottom wall of the second chamber is preferably centrally accommodated in the chamber in connection with a recess formed by the bottom wall. As a result, the fluid fraction in question is easily and quickly guided directly to the inlet opening of the channel.

Moreover, alternatively according to the invention each channel may be formed by a pipe extending rectilinearly through the piston body and being secured at the ends in the top wall of the first chamber and the bottom wall, respectively, of the second chamber where it communicates with channel portions ending in the respective chamber.

According to the invention the first and the second chamber may in a particularly simple manner comprise a common outer cylindrical wall shaped by an outer and an inner cylinder sealingly fitting within one another and defining therebetween an axially extending channel, and the cylinders may be terminated at one end by an end wall comprising an opening allowing passage of a piston rod connected to the piston body, which piston body forms the bottom wall of the first chamber and separates the first chamber from the second chamber, and where the channel extends between the end walls of the cylinders to an opening immediately adjacent, or near, the piston rod.

The methods of the present invention as described above deal with improved processes for separating and isolating an individual blood component or a solution containing such a component. However, the present method is suitable for any procedure adaptable to a cylindrical centrifuge, wherein a first solution is treated with a catalyst or agent during centrifugation so as to deposit an intermediate form of the desired product onto the centrifuge walls, and wherein the intermediate form is thereafter redissolved with an appropriate redissolving solution in the presence of centrifugal agitation so as to provide a desired concentration of the desired product in such a redissolving solution. The method as described herein may also comprise the centrifugal separation of the first solution from another solution, i.e. plasma from whole blood. Other blood procedures which could benefit from such a method include, but are not limited to the isolation of any blood component, such as platelet-rich plasma, platelet concentrate, cryoprecipitated fibrinogen, other proteins within plasma such as thrombin, fibronectin and the like.

Preferably the blood is from a single donor and most preferably the blood is from the same person to whom the blood component will be administered.

While the present methods are hereinafter described in terms of producing a fibrin monomer solution, the scope of the invention as will be appreciated by those skilled in the art, should not be so limited.

As used herein, the term "centrifugal agitation" refers to the motion of the device where the redissolving buffer solution is introduced to redissolve the intermediate product, such as non-crosslinked fibrin polymer gel, from the outer chamber walls. Such motion or centrifugal agitation may include centrifugation to ensure that all of the exposed surface area of the gel is subjected to the redissolving solution, and includes preferably such a centrifugation followed by stop-and-start rotations in the same direction and/or stop-and-start rotations in opposite directions. Typical centrifugal agitations include, but are not limited to, 5–30 second spins, preferably 5–10 second spins, at 2,000–5,000 RPM in repeated forward/reverse cycles for any desired length of time. In the present methods, 5–10 second spins at about 3,000 RPM in repeated forward/reverse cycles for 1–2 minutes is preferred. As mentioned above, this can be preceded by a somewhat longer spin, e.g., 20 seconds or more to initially distribute the solvent.

The term "fibrin" as used herein refers to fibrin I, fibrin II or des ββ fibrin.

As discussed above, the present device incorporates at least one channel capable of transferring fluid from the bottom of the second chamber in a device as defined herein to the first chamber. This feature offers a distinct advantage in facilitating the preferred method of this invention. The prior described device and method requires that upon formation of the non-crosslinked fibrin polymer gel mass, the piston is lowered to force the remaining plasma fluid up through a conduit extending through the piston plate and into the first chamber. The piston needs to contact the liquid in the prior method. Since the gel deposited on the second chamber walls in the present method, the piston cannot be lowered sufficiently to contact the remaining plasma fluid. By providing the channel extending from the bottom of the second chamber to the first chamber and by providing an atmospheric inlet into the second chamber, the piston can be lowered just slightly and pressurize the second chamber sufficiently to force the plasma fluid up the channel and into the first chamber. As discussed above, there can be provided one or a plurality of channels which may extend through the chambers or through the outer wall. A preferred way of providing a channel in the outer wall is to form the device of two cylinders, one fitting in a sealing manner within the other. By providing one or more grooves in either the inside of an outer cylinder or the outside of an inner cylinder, the one or more channels are provided.

The present device is a single, closed, automatable device capable of converting whole blood into desired blood components, preferably autologous components, useful for example as fibrin sealants.

The device is conveniently used within a drive unit which can secure and align the device, rotate the device about its axis as required and actuate pistons and pushrods which will be understood to facilitate the movement of the piston, etc., from the description herein.

BRIEF DESCRIPTION OF THE DRAWING

Preferred embodiments of the present device and methods will now be described with reference to the drawing, in which.

DESCRIPTION OF PREFERRED EMBODIMENTS OF THE PRESENT INVENTION

Figure 1:
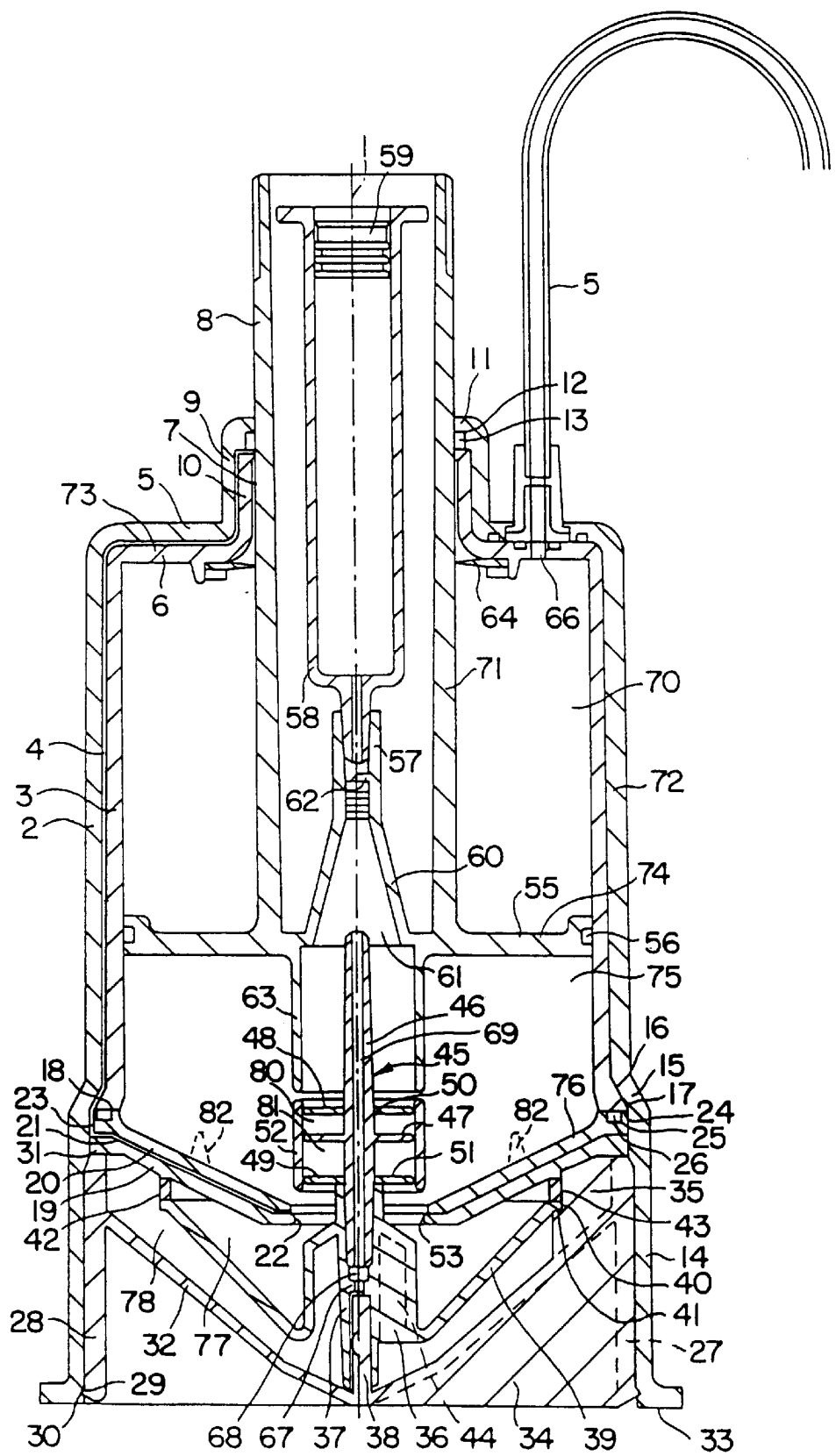
FIG. 1 is an axial, sectional view through a preferred embodiment of a device according to the invention.

The device of FIG. 1 according to the invention is built of parts substantially presenting rotation symmetry and implying that the device can be placed in a centrifugation apparatus in an easy manner known per se so as to be centrifuged about a central axis 1. In this FIG. 1, a preferred embodiment of the device comprises an outer container 2 and an inner container 3 being such that they completely fit into each other and everywhere closely abut one another apart from the portion where an axially extending intermediary channel 4 is provided. The channel 4 is provided by a groove shaped in the inner container 3. The two containers 2 and 3 comprise their respective top portions 5 and 6, respectively, which define a central opening 7 allowing passage of a piston rod 8. About the opening 7, the two containers comprise axially extending parts 9 and 10, respectively, which extend close to the hollow piston rod 8 in a direction away from the interior of the containers. The outer container 2 abuts the hollow piston rod along a short radially extending flange 11 provided with a recess 12 receiving a sealing ring 13.

As illustrated in FIG. 1, the channel 4 continues between the inner and the outer container all the way from the outer cylindrical walls of the inner and the outer container along the top portions 5, 6 and the axial parts 9 and 10 to the opening immediately below the sealing ring 13 in the opening 7. The axial part 10 of the inner container 3 abutting the opening 7 is dimensioned such that a narrow, but free passage exists to the interior of the containers 2 and 3 about the hollow piston rod 8.

The outer container 2 comprises a cylindrical part of a uniform diameter, cf. FIG. 1. Downwardly when seen relative to the drawing, this part continues into a cylindrical part 14 of a slightly larger diameter through a short transition part 15 forming a frusto-conical inner surface 16. The inner container 3 ends at the location where the transition part 15 of the outer container 2 continues into the cylindrical part 14 of a larger diameter. The lower end of the inner container 3 comprises an outer surface 17 of a frusto-conical form matching the form of the frusto-conical surface 16 on the inner side of the outer container 2. A outer and an inner annular disk 19 and 20, respectively, are provided immediately below the lower end of the inner container 3, which ends in a radial surface 18. These disks closely abut one another apart from the fact that they define therebetween a channel 21 extending in an axial plane from a central opening 22 and forwards to the inner side of the outer container 2, where the channel 21 communicates with the channel 4 between the outer container 2 and the inner container 3 through an axially extending part 23. The channel 21 and the axial channel part 23 are suitably provided by means of a groove in the side of the inner disk 20 facing the outer disk 19. The two disks 19 and 20 are shaped with such an oblique course that they comprise substantially inner and outer frusto-conical surfaces, cf. FIG. 1, and thereby incline downwards towards the central opening 22. FIG. 1 also shows that the inner disk 20 comprises a radial surface 24 abutting the adjacent radial surface 18 on the inner container 3. The radial surface 24 of the inner disk 20 is provided with a recess 25 for receiving a sealing ring 26.

The two disks 19 and 20 are maintained in position in abutment against the radial surface 18 of the inner container 3 by means of a cover 27 closing the outer container in the downward direction. This cover 27 comprises a circumferential sleeve-shaped part 28 adapted to closely abut the inner side of the outer container 2, to which it is secured in a suitable manner, such as by way of a snap-action by engagement between a circumferential rib 29 on the outer side of the sleeve 28 and a corresponding circumferential groove 30 on the inner side of the outer container 2. A sealing connection is ensured by means of a sealing ring 31 in a circumferential recess 31 a at the outer periphery of the outer disk 19. The cover 27 comprises furthermore a relatively thin wall 32 adapted to form the lower bottom of the device in the position shown in FIG. 1. This wall 32 extends substantially along a course parallel to the outer and the inner disk 19 and 20 in such a manner that the wall 32 extends from the inner side of the sleeve 28 in a portion adjacent the disks 19 and 20 and downwards towards a portion substantially on a level with the lower rim 33 of the outer container 2. In order to reinforce this relatively thin wall 32, a reinforcing radial rib 34 is provided at regular intervals, only one of said ribs appearing from FIG. 1. This rib 34 is shaped partly with a portion placed outside the wall 32 and partly with a portion placed inside the wall 32, cf. FIG. 1. The latter portion is designated the reference numeral 35 and is shaped such that it abuts the bottom side of the outer disk 19 with the result that it assists in maintaining the disks 19 and 20 in a reliable position.

A partition means 36 is squeezed between the outer disk 19 and the cover 27. This partition means 36 comprises a central pipe length 37. This pipe length is mounted on a pin 38 projecting axially inward and being shaped integral with the wall 32 of the cover 27. This pipe length 37 is shaped integral with a circumferential wall disk 39 extending outwardly from the pipe length 37 in such a manner that initially it inclines slightly downwards towards the wall 32 of the cover 27 whereafter it extends along a short axial course so as to continue into a course extending substantially parallel to the wall 32 of the cover. The wall disk 39 ends in a short radially extending periphery 40 resting on a shoulder 41 on the rib portions 35 on the cover 27. An annular filter unit 42 is squeezed between the outer periphery 40 of the wall disk 39 and the bottom side of the outer disk 19. This annular filter unit 42 abuts a substantially radially shaped surface 43 on the adjacent outer side of the outer disk 19. A device and methods employing such an annular filter are the subject of a copending application filed concurrently herewith.

In order to ensure a stability in the partition means 36, reinforcing radial ribs designated the reference numeral 44 are furthermore accommodated between the pipe length 37 and the wall disk 39 in a preferred device.

A capsule designated the general reference numeral 45 is secured in the end opposite the cover 27 of the pipe length 37 of the partition means 36. Such a capsule is suitable for delectively releasing agents into the second chamber 75 and is the object of a copending application filed concurrently herewith. This capsule comprises an elongated pipe length 46 shaped integral with a radial ring 47 and carrying two additional radial rings 48 and 49. These radial rings 48 and 49 are secured by way of interference fit on their respective side of the fixed ring 47. The loose rings 48 and 49 are accommodated at their respective distance from the fixed ring 47 by means of circumferential shoulders 50 and 51, respectively, on the pipe length 46. The three disks 47, 48, and 49 are all of the same outer diameter and carry along their respective peripheries a circumferential, displaceably mounted sleeve 52.

As illustrated in the drawing, the lower disk 49 abuts the upper end of the pipe length 37 of the partition means 36, whereby the position of the capsule 45 in the axial direction is determined. This position is furthermore determined in such a manner that when displaced in the axial direction the displaceable sleeve 52 of the capsule enters a sealing engagement by its lower end, cf. the drawing, with the innermost edge 53 on the outer disk 19 in the central opening 22. In this position of the sleeve 52, a communication still exists between the space inside the inner disk 20 surrounding the sleeve 52 and the inlet opening to the channel 21 between the outer disk 19 and the inner disk 20. The axial length of the displaceable sleeve 52 is adapted such that the engagement with the outer disk 20 occurs before the upper end, cf. the drawing, of the sleeve 52 disengages the fixed ring 47 during the axial downward displacement of said sleeve 52. The inner diameter of the sleeve 52 is also adapted to the outer diameter of the axially extending part of the wall disk 39 of the partition means 36 in such a manner that a continued downward displacement of the sleeve 52 towards the cover 27 causes said sleeve 52 to fixedly engage the partition means 36 once it has disengaged the outer disk 19. The length of the axial part of the partition means 36 corresponds also to the axial length of the sleeve 52 in such a manner that said sleeve 52 in the lowermost position is substantially completely received by the partition means 36.

As illustrated in the drawing, the hollow piston rod 8 comprises a circumferential piston 55 inside the outer container 2 and the inner container 3, said piston 55 sealingly engaging the inner side of the inner container 3 through a sealing ring 56.

A Luer-coupling 57, or other suitable coupling means, is shaped inside the hollow piston rod for receiving a conventional syringe 58 with a piston-acting plug 59 for acting on the content of the syringe 58. The coupling 57 is shaped substantially as a length of pipe communicating with a central opening 61 in the piston 55 through a frusto-conical portion 60. The length of pipe 57 is provided with a radially inwardly projecting web 62 for directing the fluid leaving the syringe 58 away from an axial path and thereby round the length of pipe 46 therebelow inside the capsule 45. The latter length of pipe 46 is of such a length and such dimensions that it can sealingly engage the length of pipe 57 inside the hollow piston rod 8 when the piston 55 is in its lowermost position near the cover 27. In order to promote the above sealing connecting, the inner side of the length of pipe 57 is formed with a gradually decreasing diameter at the end adjacent the piston 55.

An axially projecting skirt 63 is formed integral with the piston 55 about the central opening 61 of said piston. This skirt 63 is shaped with such a diameter and such a length that by a suitable displacement of the piston 55 it can activate the above displacement of the displaceable sleeve 52 of the capsule 45 into the said positions in which it engages the inner rim 53 of the central opening 22 through the two disks 19 and 20 followed by an engagement of the partition means 36.

A resilient, annular lip sealing means 64 is as indicated secured about the hollow piston at the top inside the containers 2 and 3, cf. FIG. 1. This lip sealing means 64 is adapted to prevent an undesired passage of fluid from the interior of the containers 2 and 3 to the channel 4, but it allows passage of fluid when a force is applied through the piston 55.

As indicated at the top of FIG. 1, a connection is provided to a hose 65 through an opening 66 in the outer and the inner container 2 and 3, respectively. This connection is known and therefore not shown in greater detail, but it allows an interruption of the connection to the hose when desired. In addition, an air-escape opening with a suitable filter is provided in a conventional manner and therefore neither shown nor described in greater detail.

A passage 69 is provided from the area between the partition means 36 and the cover 27 and all the way upwards through the interior of the length of pipe 37 of the partition means 36 and through the interior of the length of pipe 46 of the capsule 45. This passage 69 allows a transfer of fluid to the syringe 58 from said area when the latter length of pipe 46 is coupled to the length of pipe 57 in the interior of the piston rod 8. The passage 66 is provided at the lowermost portion of the pin 38 in the cover 27 by said pin 38 being shaped with a plane, axial surface, said pin being of a substantially circular cross section. As a result, a space is provided between the pin and the adjacent portion of the inner side of the length of pipe 37. An area 67 is provided immediately above the pin 38 where the partition means 36 presents a slightly reduced inner diameter. In this manner it is possible to place a small filter 68 immediately above the said area, cf. FIG. 1, whereby the fluid must pass said filter before it enters the length of pipe 46 of the capsule 45.

The described device comprises a first annular chamber 70, which may also be referred to as a separation chamber, defined inwardly by the hollow piston 8 forming a cylindrical inner wall 71, and outwardly by a cylindrical outer wall 72 formed by the outer container 2 and the inner container 3. When in the conventional use position, cf. FIG. 1, the annular chamber 70 is upwardly defined by a top wall 73 formed by the bottom 5 and 6, respectively, of the outer container 2 and the inner container 3.

Downwardly, the annular chamber 70 is defined by a bottom wall 74 formed by the piston 55. A second chamber 75, which may also be referred to as a reaction chamber, is defined below the piston 55, said second chamber outwardly being defined by the same cylindrical outer wall 72 as the first chamber 70. Downwardly, the second chamber 75 is defined by a second bottom wall 76 formed by the outer disk 19 and the inner disk 20. The capsule 45 is centrally accommodated in the interior of the second chamber 75. A third chamber 77 is provided below the said second bottom wall 76, and this third chamber 77 is defined by the partition means 36 and the annular filter unit 42. In addition, this third chamber 77, which may also be referred to as a filtration chamber, communicates with the second chamber 75 through the passage formed by the central opening 22 in the outer disk 19 and the inner disk 20. Finally, a fourth chamber 78 is provided below the partition means 36, said fourth chamber 78, which may also be referred to as a collection chamber, being defined downwardly by the wall 32 of the cover 27 and furthermore by portions of the sleeve 28 of the cover 27 and the bottom side of the outer disk 19.

As described above, the described device is primarily suited for separation of a component, such as fibrin monomer from blood, and for this purpose the second chamber 75, or preferably the upper chamber 80 of the capsule 46, is in advance filled with a suitable enzyme, such as batroxobin. As is understood from EP-PS No. 592,242, any thrombin-like enzyme can be employed. Such enzymes include thrombin itself or any other material with a similar activity, such as Ancrod, Acutin, Venyyme, Asperase, Botropase, Crotabase, Flavorxobin, Gabonase, and the preferred Batroxobin. Batroxobin can be chemically bound to biotin, which is a synthetic substance allowing the batroxobin to be captured in a conventionally known manner by means of avidin in an avidin-agarose composition.

Accordingly, avidin-agarose is found in the lowermost chamber 81 of the capsule. Both the biotin-batroxobin composition and the avidin-agarose composition are relatively easy to fill into the respective chambers 80 and 81 inside the capsule 45 before said capsule is placed inside the device.

Finally, a syringe 58 is arranged, said syringe containing a resolubilizing solution, e.g., a pH-4 buffer prepared from an acetate diluted with acetic acid. The syringe 58 is later used to receive the desired fibrin monomer solution.

Another buffer known from the prior art can also be used. The redissolving buffer agent can be any acid buffer solution preferably those having a pH between 1 and 5. Suitable examples include acetic acid, succinic acid, glucuronic acid, cysteic acid, crotonic acid, itaconic acid, glutonic acid, formic acid, aspartic acid, adipic acid, and salts of any of these. Succinic acid, aspartic acid, adipic acid, and salts of acetic acid, e.g. sodium acetate are preferred. Also, the solubilization may also be carried out at a neutral pH by means of a chaotropic agent. Suitable agents include urea, sodium bromide, guanidine hydrochloride, KCNS, potassium iodide and potassium-bromide. Concentrations and volumes of such acid buffer or such chaotropic agent are as described in EP-PS No. 592,242.

During or immediately after the supply of blood, the piston rod 8 is pushed so far into the interior of the device that the displaceable sleeve 52 of the capsule 45 is moved downwards into a sealing engagement in the through passage through the bottom wall 76 and to the second chamber 77. As a result, access is simultaneously opened to the biotin-batroxobin composition inside the uppermost chamber 80 of the capsule. Alternatively, the uppermost chamber 80 can be opened after the plasma fraction has been transferred to the second chamber.

When the device is ready for use, a blood sample is fed into the first chamber through a needle not shown and the hose 65 in a conventional manner, said blood sample preferably being admixed an anticoagulant also in a conventional manner. During the feeding of the blood through the hose 65 and the opening 66 into the interior of the first chamber 70, air is removed from the chamber in a conventional manner. After the feeding of blood the hose 65 is removed, and the opening 66 is sealingly closed. Subsequently, the device with the blood is placed in a centrifuge which inter alia assists in sealingly compressing the various parts. The centrifuge causes the device to rotate about the axis of rotation 1. As a result of the centrifuging, the blood is separated in the first chamber 70 into a plasma fraction settling radially inside the remaining portion of the blood, said remaining portion containing the red and the white blood cells. As described ink EP-PS No. 592,242 the platelets can be present in either fraction, as desired, by varying the speed and time of centrifugation. Centrifugation speeds using the present device are typically in the range of 2,000–10,000 RPM and may be varied as required at different points within the process and as described herein and in EP 654 669.

When the interface between the plasma and the remaining portion of the blood has stabilized, i.e. when the separation is complete, a reduction of the volume of the first chamber 70 is initiated by the piston rod 8 and consequently the piston 55 being pulled out while continuing the rotation. As a result, first a possible inner layer of air passes through the channels 4 and 21 into the second chamber 75, and a further moving of the piston 55 implies that also the plasma passes to the second chamber 75. The movement of the piston 55 is stopped when the entire layer of plasma has been forced into the second chamber 75, i.e. when the interface between the plasma fraction and the remaining portion of the blood has reached the inner wall 71 of the first chamber 70. If the uppermost chamber 80 has not already been opened, this should now be carried out so that the batroxobin is released.

In the second chamber 75, the plasma fraction comes into contact with the enzyme batroxobin with the result that fibrin monomer, which polymerizes immediately to a non-crosslinked fibrin polymer, is released from the plasma fraction. This process is performed while the device is being continuously centrifuged with the result that fibrin polymer is efficiently separated from the remaining portion of the plasma fraction, the fibrin polymer being formed by the reaction of the biotin-batroxobin composition and settling as a viscous gel layer along the cylindrical outer wall 72. When this separation has been completed, the centrifuging is stopped whereby the remaining relatively fluid portion of the plasma fraction can easily be pressed back into the first chamber 70 by the piston 55 first being raised for transferring air from the first chamber 70 to the second chamber 75 followed by said piston 55 being pressed down. The fibrin polymer may remain on the outer wall or may begin to slide off but in this case the polymer slides down much more slowly than the excess liquid. Thus, this transfer of fluid can be performed relatively easily and quickly before the viscous layer with fibrin polymer reaches the opening to the channel 21. Further measures can optionally be taken in order to prevent the viscous layer from reaching the inlet of the channel 21 too quickly, such as by providing a ring of upwardly projecting teeth 82 shown by dotted lines at the bottom 76. This centrifuging/draining procedure can be carried out two or more times, as may be required, to get as much of the plasma fluid out of the fibrin polymer as is possible.

Once the remaining portion of the plasma fraction has been expelled from the second chamber 75, the displaceable sleeve 52 of the capsule 45 is further displaced downwards in such a manner that access is allowed to the lowermost chamber 81. At the same time or in connection with the latter displacement of the sleeve, the plug 59 of the syringe 58 is pressed completely downwards by means of a spindle acting from the outside in such a manner that the pH-4 buffer is transferred to the second chamber 75, which can be done while initiating a centrifugal agitation. The addition of the pH-4 buffer provides that fibrin polymer is dissolved therein, and the presence of the avidin-agarose composition in the lower chamber 81 inside the capsule 45 provides that the biotin-batroxobin composition is bound in a conventional manner by the avidin. A continued displacement of the piston 55 causes the displaceable sleeve 52 on the capsule 45 to engage the partition means 36 and to a disengage the bottom wall 76 with the result that a free access is provided to the third chamber 77. As a result, the contents of the second chamber 75 can flow freely downwards into the third chamber 77. Preferably, the redissolving is carried out during centrifugal agitation which involves centrifugation and a series of stop-and-start of forward/reverse agitation motions as defined above.

A continued centrifuging provides that the fibrin monomer solution can be separated in the third chamber through the annular filter unit 42 retaining the relatively large particles of agarose and the batroxobin bound thereto via the biotin-avidin capture system. When the fibrin monomer solution has passed into the lowermost fourth chamber 78 as a result of the above centrifuging, said centrifuging is stopped and the fibrin monomer solution is easily transferred to the syringe 58 by a renewed retraction of the plug 59, the uppermost end of the length of pipe 46 of the capsule 45 engaging the length of pipe 47 forming the connection with the syringe 58.

Since fibrin polymer is separated from the plasma fraction in the second chamber 75 during a continued centrifuging and since the fibrin monomer solution is separated in the third chamber 77 by centrifuging it is possible to achieve a relatively high yield of fibrin monomer from the blood sample in question.

The invention has been described with reference to a preferred embodiment. Many modifications can, however, be performed without thereby deviating from the scope of the invention.

Figure 2:
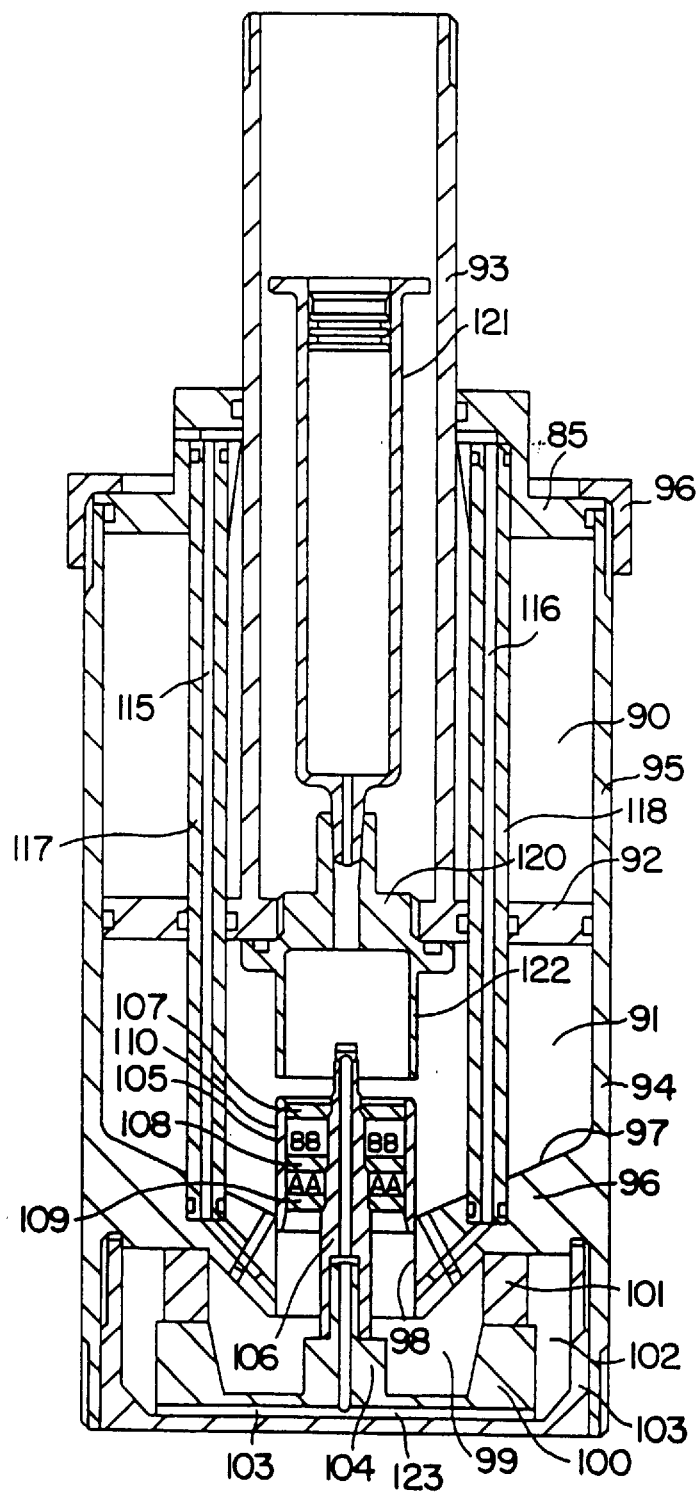
FIG. 2 illustrates a second embodiment of the device according to the invention.

FIG. 2 illustrates examples of some such modifications, wherein a second embodiment of the invention which more or less corresponds to the embodiment of the invention shown in FIG. 1 is shown. The embodiment of FIG. 2 comprises a first chamber 90 and a second chamber 91 separated by a piston 92, which comprises a hollow piston rod 93 defining the first chamber inwardly. Outwardly, the two chambers are defined by a portion of a substantially tubular member 94 forming and outer cylindrical wall 95 for the two chambers 90 and 91. Upwardly, the first chamber 90 is defined by a top wall 85 which in turn is formed by a top cover secured to the tubular member 94 by means of a ring 96 screwed into said tubular member 94. The top wall 85 defines a through opening for passage of the hollow piston rod 93. Downwardly, the second chamber 91 is defined by a bottom wall 96 formed by a circumferential inner flange in the tubular member 94. On the side adjacent the second chamber 91, the tubular member 94 comprises a frusto-conical surface 97 inclining away from the piston 92 towards the center of the second chamber 91. The bottom wall 96 defines a central through passage 98 to a third chamber 99. The third chamber 99 is defined by a partition means 100 and an annular filter unit 101 inserted between the bottom wall 96 and the partition means 100 and leading to a fourth annular chamber 102. The fourth chamber 102 is defined between a cup-shaped cover 103 secured to the tubular member 94 by threads. Said cover 103 retains through intermediary ribs 103 the partition means 100 in position centrally inside the tubular member 94 while squeezing the annular filter unit 101.

A capsule 105 is secured on a centrally and upwardly projecting pin 104 on the partition means 100. The capsule 105 comprises a tubular portion 106 with disk-shaped rings 107, 108 loosely attached thereto and defining chambers for the said enzymes indicated by the letters BB and AA, respectively, by means of a displaceably arranged sleeve. The disk-shaped rings are secured at the desired mutual distances on the length of pipe 106 by means of shoulders shaped thereon by the outer periphery of the tubular member 106 being of a decreasing diameter from below and upwards.

Through channels 115 and 116 are provided from the top of the first chamber 90 to the bottom of the second chamber 91. These channels are provided by means of their respective fixed length of pipe 117 and 118, respectively, extending parallel to the axis of rotation of the device and being secured at the ends in associated openings in the top wall 95 and the bottom wall 96. The channel connection between these lengths of pipe and the chambers, respectively, is provided by suitable bores and plugs secured therein. The lengths of pipe 117 and 118 extend through their respective opening in the piston 92. Sealing rings are provided everywhere so as to prevent leakage.

A coupling 120 is secured centrally inside the piston 92 for coupling to a syringe 121 inside the hollow piston rod 93 and to the upper end of the pipe length 106 of the capsule 105. The coupling 120 carries a skirt 122 projecting into the second chamber 91 and influencing the displaceable sleeve 110 on the capsule 105. As illustrated, the outer diameter of this sleeve 110 is adapted to the diameter of the through passage 98 downwards to the third chamber 99 in such a manner that the sleeve 110 is guided and retained by the bottom wall 96 in any position and consequently also in a lowermost position in which the sleeve 105 does not engage the lowermost disk-shaped ring 109 in the capsule and allows passage of fluid from the second chamber 91 downwards into the third chamber 99. A channel 123 extends from the fourth chamber 102 and passes centrally upwards through the pin 104 on the partition means 100 and further upwards through the tubular member 106 of the capsule 105, whereby fluid is allowed to enter the syringe 121 therefrom.

The device of FIG. 2 is used in completely the same manner as the device of FIG. 1, whereby means, of course, are also provided for coupling a hose thereto for the feeding of blood.

Figure 3:
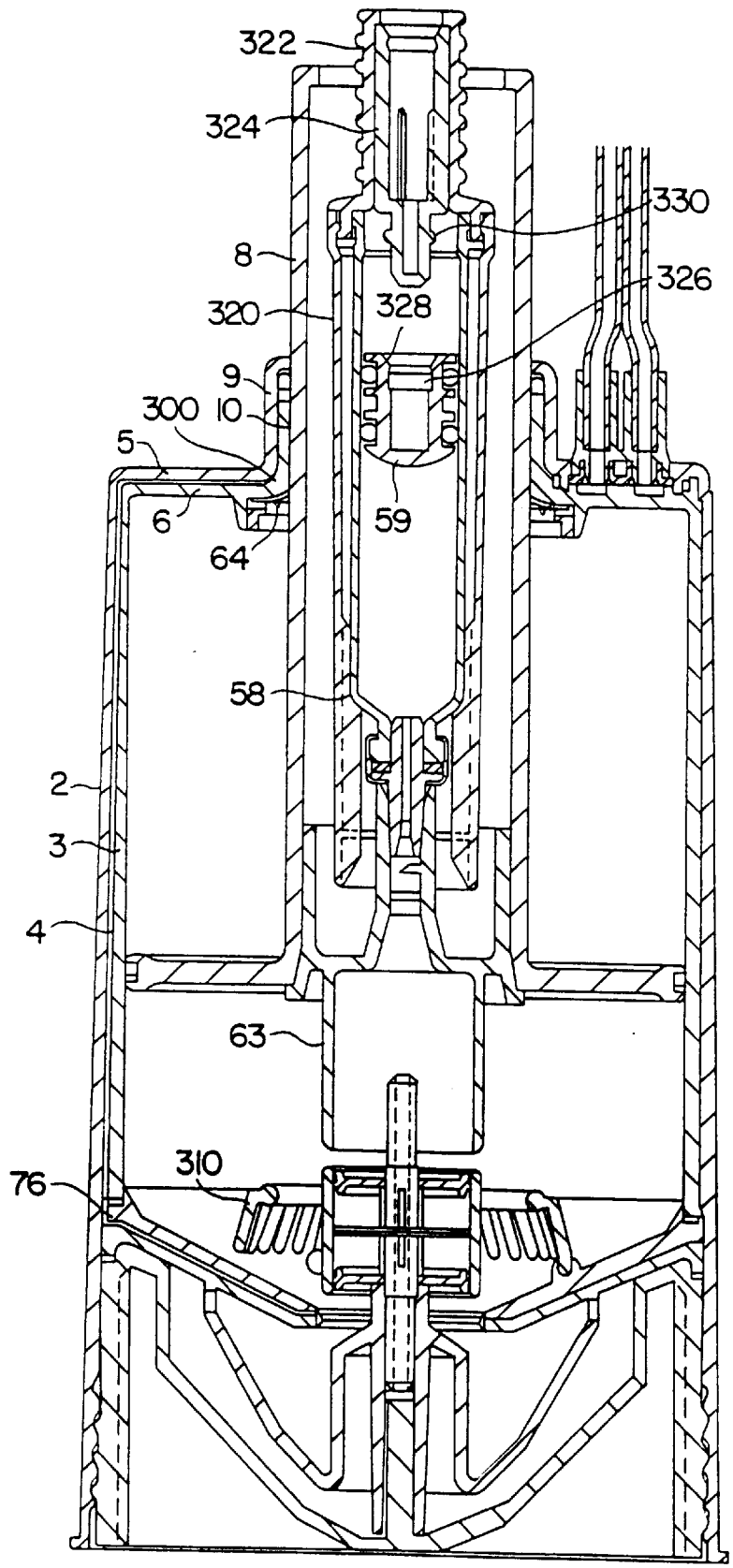
FIG. 3 illustrates a third embodiment of the device according to the invention.

Another embodiment is shown in FIG. 3 which has many of the same basic elements as FIGS. 1 and 2. The fluid transfer channel 4 is preferably formed by a slot being formed within either of the inner and outer containers 2, 3 which fit one into the other. As shown in FIG. 3, the channel 4 extends up in between the respective top portions 5 and 6 and opens into a shoulder area 300 and does not proceed between axially extending parts 9 and 10 (as in FIG. 1). The resilient lip sealing means 64 is directly adjacent the shoulder area 300 providing that the desired fluid (e.g., plasma) to be transferred past the lip sealing means 64 goes directly into the opening of the channel 4 between top portions 5 and 6 without having to travel between the portion shaft 8 and the inner axially extending part 10.

In another modification depicted in FIG. 3, the teeth 82 shown in FIG. 1 have been replaced with a "fibrin filter" 310 which is a set of teeth or tines arranged in a circular manner (e.g., on a frame or circular ring) about the capsule 45 near the bottom of the second chamber 70. The filter 310 is connected in one or more locations to the bottom wall 76 but is substantially open near the bottom wall 76 such that excess liquid can be drained off more efficiently. This arrangement helps alleviate situations using the device of FIG. 1 where fibrin polymer is retained, as desired, by the teeth 82 but where excess liquid may also be trapped behind the fibrin polymer.

Further modifications are illustrated in FIG. 3, in particular with regards to the syringe 50 where it can be seen that a protective holder 320 substantially surrounds the syringe 58. The holder 320 is preferably cylindrical or corresponds generally to the shape of the syringe 58. A holder lid 322 is releasably attached of the syringe 58 to the top of the holder 320 and provides a handle for conveniently removing the syringe 58 and holder 320 from the device after processing to provide the desired product (e.g., fibrin monomer solution) within the syringe is complete. The holder 320 can be made of a plastic or rigid polymer material so as to protect the syringe 58 during handling. Further, since the syringe is not directly touched by the operator it can be transferred to a further station for usage without contamination. A removable bottom lid (not shown) for the holder 320 may also be utilized, especially where the presterilized syringe 58 with holder 320 and containing the required acid buffer solution is provided as one component of a kit for the present device. In FIG. 3 a syringe coupler 324 is also shown which is axially slidable within the lid 322 under the action of, e.g., an upward and downward moving rod (not shown), which may be part of a drive unit for the device. The plug 59 is adapted to receive the coupler 324 in both a locking and non-locking manner. This can be accomplished, for example, by providing a recess 326 beyond a leveled receiving portion 328 within the interior of the plug 59 and a corresponding protuberance 330 on the shaft of the coupler 324. The sizes and shapes of these elements are selected such that the coupler 324 can be pushed downward with a minimal force to move the plug 59 downward without forcing the protuberance 330 past the leveled portion 320. In this way, the coupler 324 can be moved back up without changing the position of the plug 59. If a slightly greater downward force is exerted upon the coupler 324 when engaging the plug 59, the protuberance 330 will lock into the recess 326 providing that the plug 59 will now move in position with the coupler 324.

Also in FIG. 3, the axially projecting skirt 63 is shown to be a distinct component snugly fit within the bottom of the piston 55.

The parts described forming part of the various devices are easily manufactured from suitable plastic materials by way of injection molding, and the devices in question are therefore also relatively inexpensive and suited for disposable use.

Accordingly, any desired materials can be used. Preferably, gamma irradiatable stable polymers as are known in the medical device industry are employed. In a preferable embodiment the outer container and piston are of polycarbonate, the syringe holder and lids and plunger are of polypropylene, the filter is of polyethylene, the syringe is of glass, the O-rings are of silicone and the other parts are of styrene acrylonitrile.

The invention has been described with reference to preferred embodiments of the device. The method according to the invention may, however, easily be conducted in a laboratory under aseptic conditions by means of a cup which can be closed by a lid. Plasma and enzyme is filled into the cup and by mixing and following centrifugation, the non-crosslinked fibrin polymer is separated onto the bottom or the wall of the cup as described above. After removing the remaining plasma fraction, the non-crosslinked fibrin polymer is redissolved by addition of a solvent and by way of centrifugal agitation as described above as well.

EXAMPLE 140 ml of whole blood and 20 ml of sodium nitrate anticoagulant (USP) was introduced into the first chamber 70 of the device described above. This combination was centrifuged for 2 minutes at about 6,000 RPM to provide a separation of plasma and blood cells. While continuing the centrifugation to main the separation, the piston was raised so as to transfer the innermost phase, i.e. the plasma, into the second chamber 75. Approximately 60 ml of plasma was transferred. This was treated with 30 units of biotinylated batroxobin which was introduced into the second chamber 75 via the upper chamber 80 of the capsule 45 as described previously. The plasma and abroxobin were mixed at a lower speed, e.g. about 2,000 to 3,000 RPM and thereafter centrifuged for 9 minutes at 9,000 RPM.

The non-crosslinked fibrin polymer gel was precipitated as a thin gel layer onto the cylinder walls and the rotation was ceased. The remaining plasma fluid (serum) was then transferred back into the first chamber 70. This was followed by two further 1 minute centrifugations at 9,000 RPM to remove as much of the serum within the gel as possible. Following each such 1 minute centrifugation, the excess serum was transferred to the first chamber 70.

Thereafter, a buffer solution comprising 3.5 ml of a 0.2M sodium acetate (pH 4.0) containing 24 mM calcium chloride was introduced into the second chamber 75 via the syringe 58. At this time, a centrifugal agitation consisting of 5–10 second spins at about 3,000 RPMs each in repeated forward/reverse cycles was carried out for 2 minutes to dissolve the fibrin polymer gel and provide a fibrin monomer-containing solution. To the so-prepared solution was added avidin agarose via the lower chamber 71 of capsule 45. This was followed by a further centrifugal agitation consisting of 5–10 second spins at about 3,000 RPMs each in repeated forward/reverse cycles for 5 minutes. The resulting solution contained fibrin monomer plus a complex of avidin-agarose: biotin-batroxobin.

This solution was transferred into the third chamber 77 and centrifugally filtrated through a 20 μm annular Porex filter for 1 minute at 9,000 RPM. The resulting fibrin monomer solution was collected into syringe 58 as described previously and contained about 25 mg/ml of fibrin monomer.

The so-formed fibrin monomer solution (fibrin I in this case) was repolymerized into a fibrin sealant by co-administration to a site in need of such a sealant with a 0.75M sodium carbonate/bicarbonate buffer at a ratio of fibrin I:buffer of 5:1.

We claim:

1. A process for separating fibrin from plasma comprising the steps of:
    feeding said plasma into a reaction chamber defined by an outer wall, and a bottom wall;
    contacting fibrinogen within said plasma with an agent which converts said fibrinogen into a non-crosslinked fibrin polymer;
    subjecting said reaction chamber, plasma and agent to sufficient centrifugation during said contacting step so as to separate said non-crosslinked polymer from said plasma, and deposit, said non-crosslinked fibrin polymer onto said outer wall as a thin gel film.

2. The process of claim 1 for separating fibrin monomer from plasma which further comprises the step of:
    dissolving said non-crosslinked fibrin polymer by adding a solvent to the reaction chamber with the non-crosslinked polymer gel on the outer wall such that a fibrin monomer solution is provided.

3. The process of claim 2 wherein any plasma remaining in said reaction chamber after the contacting and centrifugation steps is removed from said reaction chamber prior to the dissolving of the non-crosslinked fibrin polymer.

4. The process of claim 3 wherein said plasma is removed without disturbing said non-crosslinked fibrin polymer deposited on said outer wall.

5. The process of claim 4 wherein said plasma is removed via a transfer channel having an opening in the bottom of said reaction chamber.

6. The process of claim 5 wherein air within said reaction chamber is pressurized sufficiently to force said plasma out of said chamber and through such transfer channel during said removal step.

7. The process of claim 6 further comprising the steps of:
    providing a movable top wall on said reaction chamber; and
    moving said top wall downward to reduce the volume within said reaction chamber so as to pressurize air within said reaction chamber sufficiently to force said plasma out of said reaction chamber and through said transfer channel.

8. The process of claim 2 wherein said solvent is an acid buffer solution.

9. The process of claim 8 wherein said acid buffer solution has a pH of between 1 and 5.

10. The process of claim 9 wherein said acid buffer solution is selected from the group consisting of acetic acid, succinic acid, glutonic acid, cysteic acid, crotonic acid, itaconic acid, glutonic acid, formic acid, aspartic acid, adipic acid or salts of any of these.

11. The process of claim 2 wherein said solvent is a neutral pH chaotropic agent selected from the group consisting of urea, sodium bromide, guanidine hydrochloride, KDNS, potassium iodide and potassium bromide.

12. The process of claim 2 wherein said reaction chamber, non-crosslinked fibrin polymer and solvent are subjected to centrifugal agitation.

13. The process of claim 2 wherein said fibrin monomer solution has a concentration of between 10 and 30 mg/ml of fibrin monomer.

14. The process of claim 2 wherein said plasma fluid remaining in said reaction chamber after the formation of said non-crosslinked fibrin polymer is transferred to said separation chamber prior to the dissolving of said non-crosslinked fibrin polymer with said solvent.

15. The process of claim 14 wherein said plasma fluid remaining in said reaction chamber after the formation of said non-crosslinked fibrin polymer is transferred to said separation chamber via one or more transfer channels extending from the bottom of said reaction chamber into said separation chamber.

16. The process of claim 15 wherein said one or more transfer channels extend from the bottom of said reaction chamber to the top of said separation chamber.

17. The process of claim 1 wherein fibrin is fibrin I, fibrin II or des ββ fibrin.

18. The process of claim 1 wherein said agent catalyzes the cleavage of fibrinopeptides A and/or B from fibrinogen and is selected from the group consisting of thrombin, Ancrod, Acutin, Venyyme, Asperase, Botropase, Crotabase, Flavorxobin and Gabonase.

19. The process of claim 1 further comprising the steps of:
    feeding blood into a separation chamber;
    subjecting said separation chamber to a centrifugal force sufficient to provide for the concentric separation of a more dense blood cell phase and a less dense plasma phase; and
    maintaining said centrifugal force while feeding said plasma into said reaction chamber.

20. The process of claim 19 wherein said separation chamber has an anticoagulant material therein.

21. The process of claim 19 wherein said separation chamber and said reaction chamber are aligned about a common axis in a unitary device.

22. The process of claim 21 wherein a movable piston separates said chambers and constitutes a top wall of said reaction chamber and a bottom wall of said separation chamber.

23. The process of claim 1 wherein said agent is present in said reaction chamber prior to feeding of said plasma.

24. The process of claim 1 wherein said agent is introduced into said reaction chamber after feeding of said plasma.

25. The process of claim 1 or 16 for separating any polymerizable or precipitatable component from within blood or plasma wherein said agent is capable of converting a substance within said blood or plasma into said component.

26. The process of claim 1 or 16 wherein said solvent is capable of dissolving said component to provide a solution thereof.

27. The process of claim 19 for separating any polymerizable or precipitatable component from within blood or plasma wherein said agent is capable of converting a substance within said blood or plasma into said component.

28. The process of claim 19 wherein said solvent is capable of dissolving said component to provide a solution thereof.

29. A process for separating a fibrin monomer solution from blood comprising the steps of:
    feeding blood into a cylindrical separation chamber defined by an outer wall, a top wall and a moveable piston as the bottom wall;
    rotating said separation chamber about its longitudinal axis so as to provide a centrifugal force sufficient to cause the concentric separation of a plasma fraction and a cell fraction;

feeding the so-separated plasma through a transfer channel, while continuing said rotation, to a cylindrical reaction chamber aligned along the same axis as said separation chamber, said reaction chamber further defined by a bottom wall, a common outer wall with said separation chamber and said piston as a top wall, said transfer channel extending from the bottom of said reaction chamber into said separation chamber, said feeding being provided by an upward motion of said piston which reduces the volume of the separation chamber thereby forcing said plasma through said transfer channel;

contacting said plasma with an agent capable of converting fibrinogen within said plasma into a non-crosslinked fibrin polymer, said contacting be carried out during continued rotation so as to deposit said non-crosslinked fibrin polymer onto said outer wall of said reaction chamber;

stopping said rotation so that remaining plasma fluid drains to the bottom of said reaction chamber;

pressurizing the air within said reaction chamber sufficiently and moving said piston slightly downward so that said remaining plasma fluid is forced back up into said transfer tube and into said separation chamber, whereby said non-crosslinked fibrin polymer is substantially undisturbed by said slight piston movement;

introducing a solvent into said reaction chamber; and agitating said reaction chamber so that said solvent dissolves said non-crosslinked fibrin polymer to provide a solution comprising fibrin monometer and said solvent.

* * * * *